United States Patent [19]
Kuhls

[11] Patent Number: 5,687,721
[45] Date of Patent: Nov. 18, 1997

[54] MEASUREMENT DEVICE FOR NON-INVASIVELY DETERMINING THE CONCENTRATION OF POLARISING SUBSTANCES

[76] Inventor: Burkhard Kuhls, Mitterhoferstrasse 19, 2-80687 München, Germany

[21] Appl. No.: 464,657

[22] PCT Filed: Dec. 14, 1994

[86] PCT No.: PCT/DE93/01193

§ 371 Date: Jun. 15, 1995

§ 102(e) Date: Jun. 15, 1995

[87] PCT Pub. No.: WO94/13193

PCT Pub. Date: Jun. 23, 1994

[30] Foreign Application Priority Data

Dec. 15, 1992 [DE] Germany .................. 42 42 232.9

[51] Int. Cl.$^6$ ........................................ A61B 5/00
[52] U.S. Cl. ........................... 128/633; 356/364
[58] Field of Search ........................ 128/633, 634, 128/664, 665; 356/364, 367, 368, 369

[56] References Cited

U.S. PATENT DOCUMENTS

| | | | |
|---|---|---|---|
| 3,877,816 | 4/1975 | Weiss | 356/138 |
| 5,009,230 | 4/1991 | Hutchinson | 128/633 |
| 5,357,960 | 10/1994 | Schmidtke et al. | 128/633 |

FOREIGN PATENT DOCUMENTS

| | | |
|---|---|---|
| 0282234 | 3/1988 | European Pat. Off. . |
| 63293442 | 11/1988 | Japan . |
| 9007905 | 7/1990 | WIPO . |
| 9207511 | 5/1992 | WIPO . |

*Primary Examiner*—Jennifer Bahr
*Assistant Examiner*—Eric F. Winakur
*Attorney, Agent, or Firm*—Wigman, Cohen, Leitner & Myers P.C.

[57] ABSTRACT

A device and method are disclosed for noninvasively measuring the concentration of sugar in the blood of a human subject. The method includes generating a beam of monochromatic light, confining the light beam to a predetermined optical path to impinge on a preselected portion of the body of the subject, polarizing the light beam, and performing both a static extinction measurement using the monochromatic light and a dynamic polarization measurement using the polarized light to obtain a measurement of the concentration of sugar in the blood in the preselected body portion. The dynamic polarization measurement is performed by analyzing the polarized light beam after impingement on the body portion while rotating the beam to produce a measurement signal indicative of the angle of polarization thereof, generating a reference signal indicative of influence of rotation of the beam on the angle of polarization thereof in the absence of blood in the optical path, and comparing the measurement signal and the reference signal to determine the angle of deflection of the light beam attributable to the presence of blood sugar in the optical path as a measure of the concentration of sugar in the blood flowing through the body portion.

21 Claims, 13 Drawing Sheets

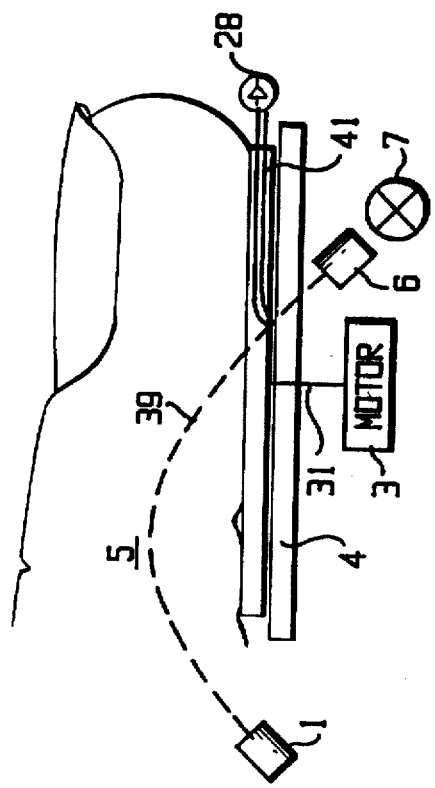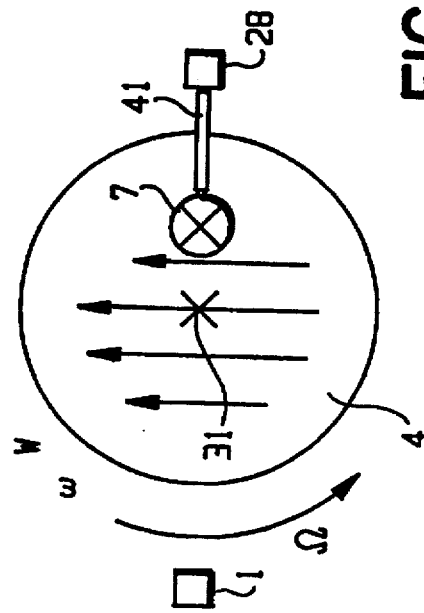
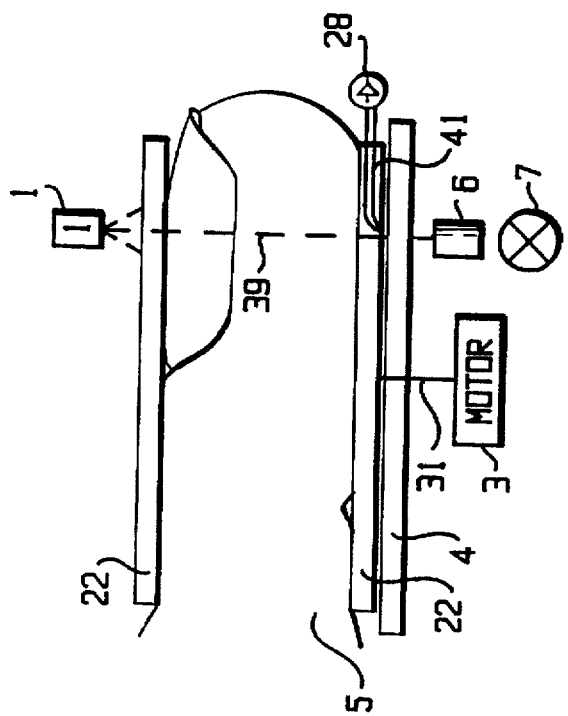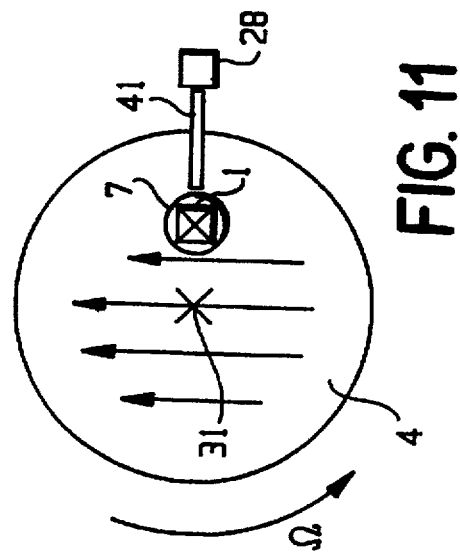
FIG. 11
FIG. 12
REMISSION

REMISSION

TRANSMISSION

REMISSION

TRANSMISSION

REMISSION

DEMODULATOR VARIANT

DEMODULATOR VARIANT

PHASE VARIANT

PHASE VARIANT

MEASUREMENT DEVICE FOR NON-INVASIVELY DETERMINING THE CONCENTRATION OF POLARISING SUBSTANCES

SUMMARY OF THE INVENTION

Device for noninvasive measurement of polarizing substances in human blood, particularly for the measurement of blood sugar concentration by determination of the optical rotation, consisting of a light source, a periodically rotating polarizer/analyzer in combination with an angle sensor to determine the rotational frequency of the polarizer, a body part as measurement object arranged within the beam of the light emitted, and a photodetector, as well as an electronic assembly to determine the blood sugar concentration from the measured values obtained.

The periodically rotating polarizer converts the angle of rotation of the polarization into a phase angle of the intensity curve of the transmitted light. Through measurement of the phase shift through the object to be measured with respect to the reference phase as well as through a static extinction measurement (tissue and blood) and a dynamic measurement (only the pulsating part of the blood), the blood sugar concentration can be noninvasively determined. The measurement may be a transmission measurement or a diffraction measurement.

This device, with a sensor system, is capable of performing two independent measurements simultaneously (phase modulation and extinction measurement). Maximum suppression of noise and interference affecting the electronic assembly for assessment can be achieved through freely selected modulation frequency.

When too much sugar is in the human blood, insulin is released from the pancreas. This insulin is distributed in the blood and causes the cell membranes of all cells reached to become more conductive for glucose absorption. In this way, the blood sugar content drops, since the cells absorb and utilize the sugar (glycolysis for cell support; glycogen synthesis in the liver). Diabetics have permanently elevated blood sugar values (diabetes mellitus) because of insulin deficiency. This is one of the most common diseases of modern civilization and causes permanent damage to the eyes (for example, blindness), kidneys, vascular system, nervous system, and even loss of extremities. Due to a defective intrinsic regulatory system, the life of the diabetic is shortened, with all of the above consequences. The normal blood sugar value is 0.7 to 1.1 g/L. Depending on nutrition, the diabetic sometimes lies considerably above the normal value, so that frequently, the return to a normal blood sugar value is achieved only through injection of insulin. So that the diabetic is well adjusted, he must regularly check his blood sugar value and, if necessary, inject insulin. A control measurement every 2 min would be the optimum. The usual methods measure in vitro, in that the diabetic must pierce the fingertip with a lancet. The next step is to put a drop of blood on a test strip, where an enzymatic reaction takes place. After approximately 30 sec, the diabetic obtains, through an electronic measuring device, his blood sugar value displayed digitally. The assessment occurs through the conductivity or through photometric measurement. The blood measurement method is a great burden for the diabetic for reasons of hygiene and time. Particularly important for the diabetic is the sugar determination before meals. Based on the blood measurement method, this cannot be done in public (pubs, restaurants, . . . ).

To determine sugar in the urine, a polarimeter (also called saccharimeter[1]) is used. Sugar is optically active. When linearly polarized light passes through such substances, the polarization direction rotates around the beam axis. In solutions of optically active substances, the angle of rotation $\alpha$ is proportional to the concentration, and thus: $\alpha=\alpha_0*C*d$, wherein d is the thickness of the solution layer penetrated and $\alpha_0$ is a substance constant which is called the specific rotation.[2] A polarimeter consists essentially of two polarizers, of which the one facing the detector is called the analyzer. If the transmission directions of polarizer and analyzer are oriented vertically to one another (crossed position), light that oscillates in the polarizer direction cannot pass the arrangement; all is dark. If a cuvette filled with an optically active solution is introduced between the polarizer and the analyzer, the polarimeter becomes transparent[3] for the intensity portion $I=I_{max}*\sin^2\alpha$. By rotating the analyzer back to darkness, the angle of rotation $\alpha$ of the optically active sample can be determined, and from this and from the light path (cell path d), the sought concentration as well. Another possibility is sugar determination in the urine through test strips that change color. This method is limited by the fact that the kidneys normally completely reabsorb glucose from the urine. Only with a blood sugar level over 1.8 g/L is glucose eliminated in the urine.

[1]Bergmann: Textbook of Experimental Physics, Vol. III, Optics, p. 523.
[2]Trautwein: Physics for Doctors, Biologists, Pharmacists, 4th edition, p. 348.
[3]Bergmann/Schaefer: Textbook of Experimental Physics, Optik, Vol. III, 7th edition, p. 451 "Malus' Law"

The most frequent practically applied methods are, without exception, in vitro methods. These are small, handy devices where two distinct measurement principles are applied.

The "Glucometer II Model 5526," requires a "Glucofix" test strip, which has test fields where the drops of blood must be placed. Two different test fields are located next to each other, one for a low and the other for a high glucose concentration. After approximately 30 sec, the reaction is interrupted in that the drops of blood are wiped off. Now, the glucose concentration can be determined by comparison with a color table or the device determines the blood sugar value by a photometric measurement.

The "Exatech" is currently the newest device. It can be obtained in the check card or ballpoint pen format. A test strip is put into the device. After application of a drop of blood, the device can be started. From the beginning, enzymatic reactions occur on the test strip, whose course is measured through the conduction value. After approximately 30 sec, the LED display gives the blood sugar value determined.

The devices have a limit of error of up to 50%. It is remarkable that the business concerns not so much the devices themselves, but rather the test strips. On average, one test strip costs DM 1.50.[4] A diabetic uses up to 5 strips daily so that the annual cost is DM 2,700.00.

[4]Journal "Test": "Fix, and fast perfect," of September 1992, p. 82.

In Albuquerque (U.S.A.), spectral analysis (with infrared light) was first used successfully to measure blood sugar noninvasively.

The latest state of the art is represented by U.S. Pat. No. 5,009,230 of Apr. 23, 1991. This is a polarimeter which is switched in a defined manner. Through the subtraction of two different analyzer adjustments, an angle of difference is measured corresponding to the change of intensity, which is proportional to the glucose concentration. The measurement can be made noninvasively at different wavelengths as a transmission measurement.

The device according to this patent specification (U.S.

Pat. No. 5,009,230) also has two polarizers which measure the transmitted light energy. But there are the following disadvantages:

Through the switching, according to Fourier, infinitely many harmonic waves are theoretically present in the measurement signal in such a "rectangular pulse," so that the energy, particularly in the case of rapid switching sequences, is distributed over the whole spectrum. In the case of such a small polarization angle as that produced by blood, the measurement signal is obscured by noise. Because the noise output is dependent upon the bandwidth of the allowed spectra, the measurement value can hardly be identified using it.

The measurement device is limited to a transmission measurement, so only body parts which can be directly irradiated can be considered.

The object of the invention consists particularly of being able to determine the blood sugar concentration in a noninvasive manner. Insurance companies show that untrained diabetics cause, annually, approximately DM 15,000 more treatment costs than "well adjusted" diabetics (DM 1000–4000).[5] For this, a device has been used which optically determines the rotation of the polarization plane through a polarimeter. In this way, it is easier for the diabetic to become "well adjusted." This object is attained by a measurement device consisting of a light source, a periodically changing polarizer, a photodetector, and an electronic assembly for determination of the blood sugar concentration from the measured values obtained.

[5]Hamburger Abendblatt/Ditrich: "When thirst is dangerous" of Aug. 29, 1992, Second World Diabetes Day in Potsdam Blood sugar is a monosaccharide and is represented as D-(+)-glucose.[6] Linearly polarized light is rotated to the right (clockwise) from its original polarization direction by dissolved blood sugar due to its optical activity. In solutions of optically active substances, the angle of rotation $\alpha$ is proportional to concentration C, and the following applies:

$$\alpha = \alpha_0 * C * d \tag{1}$$

wherein the meanings are:
- C: concentration of the optically active substance (here: blood sugar);
- $\alpha$: angle of rotation of the polarization direction dependent upon the layer thickness in each case;
- $\alpha_0$: specific rotation; (determine as much as possible in blood);
- d: rotating layer thickness.

[6]Schröter/Pocketbook of Chemistry, 9th edition, p. 505

The device according to the invention makes it possible to continuously determine particularly the blood sugar concentration through polarization and extinction in the dynamic pulsating blood, in a noninvasive manner, with low polarization. A high precision of the measurement device is achieved. Assuming an average blood layer thickness, for example, in the finger of 2 mm the plane of rotation (raw sugar: $\alpha_0 = 66.5°/dm°$)[7] by approximately 0.013° with a normal blood sugar value of 1 g/L (100 mg/dL). That is, with a measurement precision of 10%, a precision of 1/1,000° is required. The periodically rotating polarizer converts the angle of rotation of the polarization into a phase angle of the intensity curve of the transmitted light. By measuring the phase shift through the measurement object with respect to the reference phase, the blood sugar concentration can be determined in a noninvasive manner both through a static extinction measurement (tissue and blood) and a dynamic measurement (only the pulsating portion of the blood). The measurement can be a transmission measurement or a diffraction measurement.

[7]Bergmann/Schaefer: Textbook of Experimental Physics, Optics, Vol. III, 7th edition, p. 519

Polarized light is input into the measurement object (for example, finger, earlobe). It is put out through an analyzer rotating at frequency f (FIG. 2) or by use of magnetic rotation (for example, Faraday effect) through a magnetic field oscillating at $\Omega$. The analyzer converts the angle of rotation of the direction of oscillation into a phase angle of the intensity curve of the transmitted light. The order of analyzer/measurement object is inconsequential for the measurements.

Here, the polarized light is modulated, for example, sinusoidally, through the periodic effects of force on the analyzer/polarizer. Through the periodic polarization rotation (modulation) of the analyzer or polarizer, the following possibilities, for example, exist:

- through mechanical rotation (rotation drive) the polarization direction is changed:
  - polarization films (film of transparent plastic with miscellenea)[8];
  - cellulose hydrate films (by stretching, an oriented strain double refraction is elicited)[9];
- through a magnetic field, the polarization direction can be changed:
  - magnetic rotation (Faraday effect): the polarization direction is rotated through a magnetic field (for example, lead silicate glass, rock salt)[10];
- the polarization direction is periodically changed through an electric field:
  - polarization direction is rotated by application of an external electric field.

[8]Pohl: Optics and Atomic Physics, 13th edition, p. 116
[9]Bergmann/Schaefer: Textbook of Experimental Physics Optics, Vol. III, 7th edition, p. 515.
[10]Bergmann/Schaefer: Textbook of Experimental Physics, Optics, Vol. III, 7th edition, p. 572

For the intensity transmitted by the analyzer, for example, with sinusoidal modulation, the following applies:

$$I_{analyzer} = I_{max} * \sin^2(\Omega t - \alpha)$$

$I_{max}$ = maximum of the transmitted intensity
or according to application of the addition theorems:

$$I_{analyzer} = I_{max}/2 * [1 - \cos(2\Omega t - 2\alpha)]$$

The intensity of the transmitted light oscillates accordingly with the doubled rotation frequency $\omega(=2*\Omega)$.

The transimpedance amplifier (TIV) supplies, therefore, the starting voltage:

$$Ua(TIV) = U_{max} * [1 - \cos(\omega t - 2\alpha)],[11]$$

where $U_{max}$ corresponds to the maximum intensity $I_{max}$.

[11]Journal "Elektronik": "Lock-in measurement technique with digital signal assessment," Volume 2/Jan. 25, 1985, p. 67 (formula expanded by the polarization angle: $-2\alpha$)

The angle of polarization $\alpha$ is rotated through the optically active blood sugar.

Diffraction influences the prevailing polarization direction only in that the prevailing direction of polarization is constructed deterministically, and thus, the signal is more difficult to identify.

Synchronously with this, the frequency and phase position are measured as references through an angle sensor. Using this reference measurement, the intrinsic signal which results from the measurement object can be compared and assessed. The angle sensor can work electrically, optically, or magnetically.

As polarizing light source, semiconductor laser diodes are available. Above the threshold current, laser diodes emit linear polarized light at a polarization plane which is parallel to the pn junction. Since, however, a portion of the radiation is from spontaneous emission, the purity of the polarization is never 100%. With increasing laser capacity, this value also increases.[12] In the above-used device, primarily polarized light is sufficient for detection. Fully polarized light as light source through the polarizer (for example, with film or Brewster window) can, however, increase the signal-to-noise ratio.

[12]Stratis Karamanolis: The ABCs of Laser Technology, p. 79

An angle sensor/phase sensor is used as reference. This is measured directly at the output of the motor, polarizer, analyzer, or by the function generator. A detector determines optically (reflex or transparent), magnetically, electrically, or electrostatically, the transient phase position.

Both polarization as well as extinction are used for assessment. In order to measure, as much as possible, noninvasively, the pulsating blood itself, the fact is exploited that with a dynamic measurement (only blood pulsation) considerable blood itself is recorded.

For extinction measurement, monochromatic light is measured. The extinction can fluctuate greatly at wavelengths between 600 nm to 780 nm since here, it is dependent upon the transient oxygen saturation in the blood. In order to be able to carry out measurements independently of the oxygen saturation in the blood, wavelengths at the "isobestic points" around 550 nm and 805 nm are particularly suitable.

To meet safety-technical requirements, the carrier signal and the information can also be conducted back and forth to the measurement object by means of polarizing waveguides. The rotating disk modulates the polarized light thereby, either directly at the measurement object or externally.

The apparatus can also be constructed in subminiature form, wherein it can also be used invasively as a transplant.

The measurement values obtained from the apparatus described above are coded for the noninvasive glucose determination by electronics or using a program according to the following scheme:

The measurement apparatus is calibrated with a known blood sugar concentration C1 on the subsequent measurement object by means of a calibration measurement. The following is valid:

α: angle of the rotation of the polarization plane (produced by the optically active substance→here: glucose)

C: blood sugar concentration $k_{pol}$: tissue polarization (constant; not dependent on the blood pulsation)

d: effectively acting layer thickness of the blood vessel

Δd: pulse stroke (only the dynamically pulsating portion of the blood vessel)

$$\alpha = \alpha_{10} * C * d + k_{pol} \text{ Polarization angle} \quad (8)$$

In order to detect the blood sugar present in the blood, only the dynamic angle changes brought about by the blood pulse are used.

The following is valid for small $\Delta d_{vessel}$:

$$\frac{\Delta \alpha}{\Delta d} = \frac{\partial \alpha}{\partial d} = \alpha_0 * C$$

-continued $$\Delta \alpha = \Delta d * \alpha_0 * C \quad (10)$$

wherein $k_{pol}$ disappears.

After calibration with concentration $C_1$, for an unknown concentration $C_{measurement}$, the following applies:

$C_{meβ}$:

$$\frac{\Delta \alpha_{meβ}}{\Delta \alpha_1} = \frac{C_{meβ} * \Delta d_{meβ}}{C_1 * \Delta d_1}$$

bzw:

$$C_{meβ} = C_1 * \frac{\Delta \alpha_{meβ} * \Delta d_1}{\Delta \alpha_1 * \Delta d_{meβ}} \quad (12)$$

Key: 1 Measurement
     2 Or

Here, the pulse strokes Δd shorten completely only for identical circulatory values (blood pressure, pulse, etc.). In general, however, the ratio $\Delta d_1/\Delta d_m$ must be determined as a function of the individual circulatory parameters, for example, in the form of a calibration curve. This can be circumvented when the pulse strokes are determined by an additional extinction measurement.

From the Lambert-Beer equation, by differentiation according to the layer thickness d, the following is obtained:

$I_{in}$: irradiated intensity $I_{measurement}$: measured intensity $C_{hem}$: hematocrit concentration; in the blood (men: 510 g/L[13] or 0.47 mL cells/dL blood[14]; women: 460 g/L or 0.42 mL cells/dL blood)

d: effective layer thickness of the blood vessels

Δd: pulse stroke (only of the dynamically pulsating portion of the blood vessel)

ε: extinction coefficient of the hematocrit at the wavelength to be measured $a = C_{hem} * \epsilon$ $k_{loss}$: loss by tissue absorption and tissue diffraction (constant; not influenced by blood pulsation)

$$I_{measurement} = I_{in} * e^{-d*a - k(loss)} \quad (14) \text{ Lambert-Beer law}$$

[13]Thews, Vaupel: Foundations of Vegetative Physiology, 1981, p. 22
[14]Schmidt Thews: Human Physiology, 23rd edition, p. 422 and it follows for the small $\Delta d_{vessel}$:

$$\frac{\Delta I}{\Delta d} = \frac{\delta I}{\partial d} = -a * I_{meβ}$$

$$\Delta d = -\frac{\Delta I}{a * I_{meβ}} \quad (16)$$

Key: 1 Measurement

If the ratio between calibration value $\Delta d_1/\Delta d_{measurement}$ is formed and inserted into the above formula, the following is obtained:

$$C_{meβ} = C_1 * \frac{\Delta \alpha_{meβ} * \Delta I_1 * I_{meβ}}{\Delta \alpha_1 * \Delta I_{meβ} * I_1} \quad (18)$$

from 12 and 16
Key: 1 Measurement

The possibility of expressing the pulse stroke through the appropriate extinction leads to a further method which can be done without calibration measurement. The following applies:

$$\Delta\alpha_{me\beta} = C_{me\beta} * \alpha_0 * \Delta d_{me\beta} \quad (20)$$
from (10)

$$\Delta d_{me\beta} = \Delta I_{me\beta}/(I_{me\beta} * -a_{Blut}) \quad (22)$$
from 16

$$C_{me\beta} = \frac{\Delta\alpha * I_{me\beta} * a_{Blut}}{\alpha_0 * |\Delta I|} \quad (24)$$

from 20 and 22)

Key: 1 Measurement
     2 Blood
     3 From
     4 And and extended at $1/\Delta t$, clearly yields a ratio of two temporal slopes:

$$C = \frac{\frac{\Delta\alpha}{\Delta t} * a * I_{me\beta}}{\frac{|\Delta I|}{\Delta t} * \alpha_0} \quad \text{Blutzucker-Konzentration} \quad (26)$$

Key: 1 Measurement
     2 Blood sugar concentration

Practically speaking, this means that two slopes are measured and put into a relationship with one another. The expression $\Delta\alpha/\Delta t$ describes the tangent slope of the polarization and $\Delta I/\Delta t$ the tangent slope of the light intensity. For the measurements, a general reference point is required by which the slope is determined. For this, the inflection point at the rising pulse is recommended. Losses due to diffraction, input, losses in light wave conduction, are multiplicative, both in the $I_{measurement}$ as well as in the $|\Delta I|$, and also, therefore, reduce.

With experimentally determined factor $a/\alpha_0$, the blood sugar concentration can be determined with only one radiator and one detector (and a reference) using this formula.

Instead of the above-described transmission measurement, a reflectance measurement is also possible. The device could also be worn, for example, like a wristwatch. The polarized light is irradiated sideways into the tissue. By diffraction, the photons return to their path again outside the tissue. In spite of diffraction, the reference orientation of polarization is maintained. It is only rotated through the optically active substance (here, blood sugar).

With the reflectance measurement, it should be observed that two different paths must be considered for the polarization and for the extinction, so that correction factor k is required.

For the average path of extinction, for reflectance, it applies that the photons which arrive in the tissue from their radiation direction move almost in a half-circle on the IR detector.

For the average path of polarization, for reflectance, it applies that for the rotation of the vibration direction of the arriving photons, only the shortest connection between source and sensor in the tissue can be used as a basis, because the "detours" are compensated such that, for example, on the outward path and the return path, opposite rotations occur so that the latter are eliminated.

In order to make the path correction factor as close as possible to "1" in reflectance, the device must be constructed so that the radiating light beam penetrates as much as possible only shallowly into the tissue so that the effective paths for extinction and polarization hardly can be distinguished from one another. Such a reflectance measurement corresponds almost to a transmission measurement.

In order to compensate for the measurement precisions, for example, by moving the armband device, several similar detectors and senders can be applied simultaneously. For this, the senders are switched on individually one after the other. The corresponding IR detectors measure the incoming intensities or polarizations (with consideration of the predetermined intervals) at the same time. The multiple radiation measurement method gives individual irregularities (inhomogeneities in the tissue, "deaf" senders, "blind" receivers) are compensated for.

The advantages of this solution are that the high precision required for determination of the polarization angle here is dependent now only upon the resolution of the angle code/angle sensor, that is, the reference. The advantage over systems which measure by discrete time (such as, for example, the above-mentioned U.S. Pat. No. 5,009,230) is that the requirement of assessment teletronics can be very much less. With continuous, that is, sinusoidal modulation, the information sought is only in this modulation frequency, so that all other frequencies can be filtered out and thus, the small signal can be intentionally intensified from the noise.

By modulation of the signal to a frequency which is convenient for the assessment teletronics, a lower 1/f noise results from the assessment teletronics (for example, convenient for operation amplifiers in the range of 100 Hz to 30 khz) in contrast to systems which measure by discrete time.

Through this combination of the polarization measurement (through phase modulation here) with an extinction measurement, two independent measurements per light wavelength are made through one and the same sensor. Thus, material and balancing effort by the electronics are saved.

The combination of both measurements makes possible already a tissue-independent blood sugar determination. Therefore, instead of one transmission measurement, one diffraction measurement (reflectance measurement) suffices for blood sugar determination. The method according to the above-mentioned U.S. Pat. No. 5,009,230 works only reasonably noninvasively with known layer thickness or at least two measurement systems.

Through the noninvasive measurement method, it results that the measurement is painless and not infectious. When critical blood sugar values appear, the diabetic is warned directly by the device. Another advantage of the method is that the blood sugar measurements after a while are considerably cheaper than the daily use of test strips (up to 5*DM 1.50 daily). In particular, older diabetics frequently suffer from visual weakness and therefore cannot easily handle the conventional devices. Through the measurement device described (for example, as a wristwatch device), the problems resulting from this can be avoided.

BRIEF DESCRIPTION OF THE DRAWINGS

In the drawings, the invention is illustrated in different embodiment forms as examples. Shown are:

FIG. 11, a variant in which the reference measurement is done directly behind the polarizing disk, where the light is directed through a waveguide to the reference detector or this detector is attached directly behind the polarizing disk. The waveguide behind the analyzer does not need to receive polarization. The reference track is the polarizing disk itself in this case.

FIG. 12, a device which takes a diffraction measurement (reflectance measurement) through the tissue. The optical detector here is on the same side as the light source with respect to the measurement object.

DESCRIPTION OF THE PREFERRED EMBODIMENT

Figure 1:
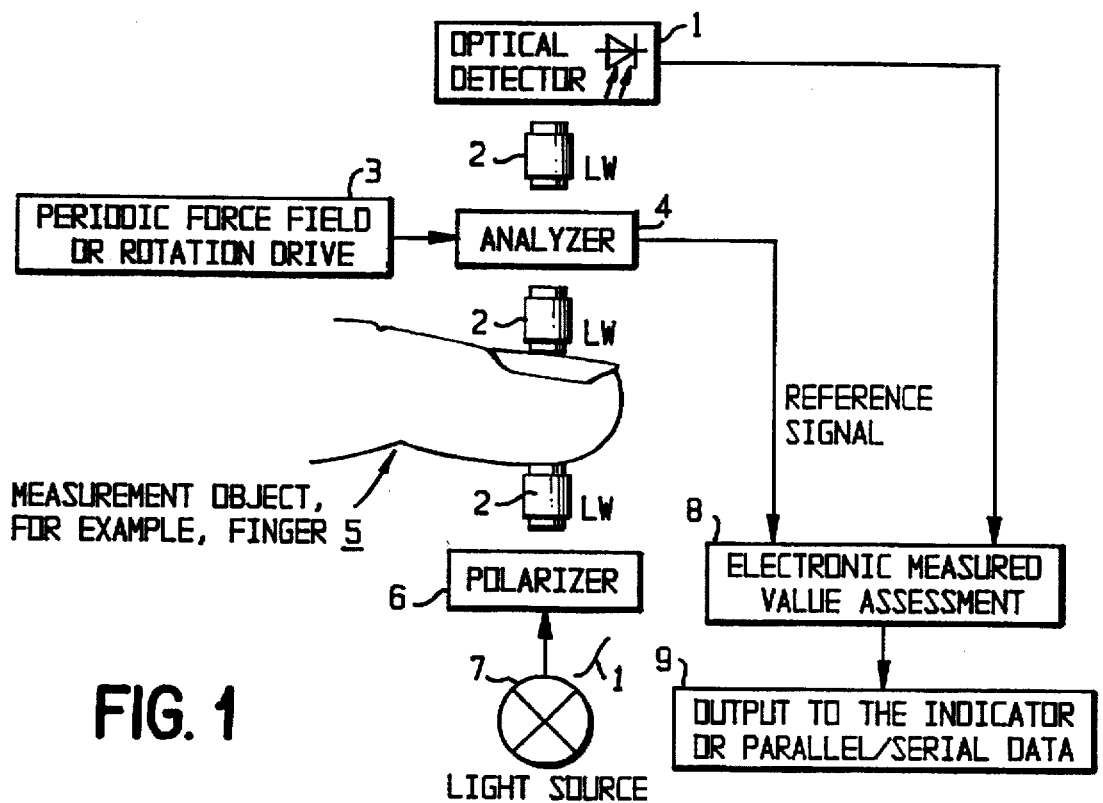
FIG. 1, schematic of the arrangement of the measurement device in the following order of assembly: light source, polarizer, measurement object, periodically changing analyzer, reference signal from the analyzer, optical detector, and the electronic measurement assessment. Aside from the polarization, through the measurement electronics, the extinction is also evaluated in that, as much as possible, monochromatic light is measured (the more monochromatic the measurement system is constructed, the better the signal-to-noise ratio).
Figure 2:
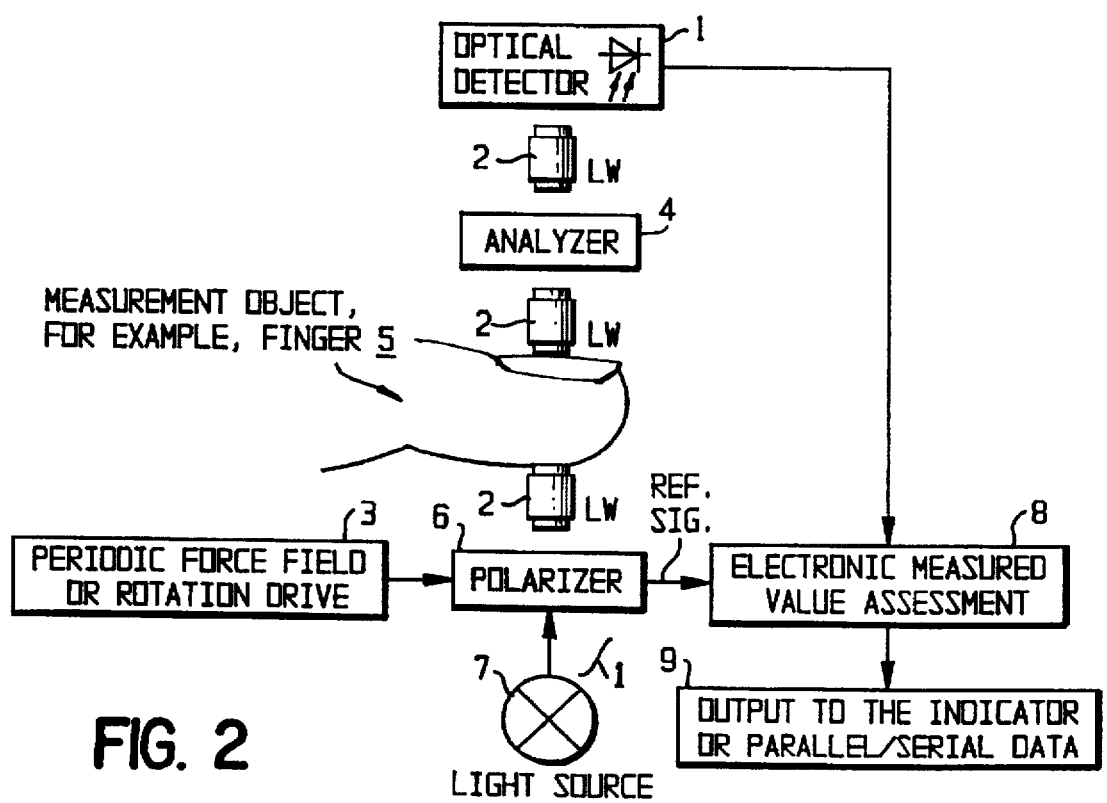
FIG. 2, as an alternative, a periodically changing polarizer instead of the periodically changing analyzer.
Figure 3:
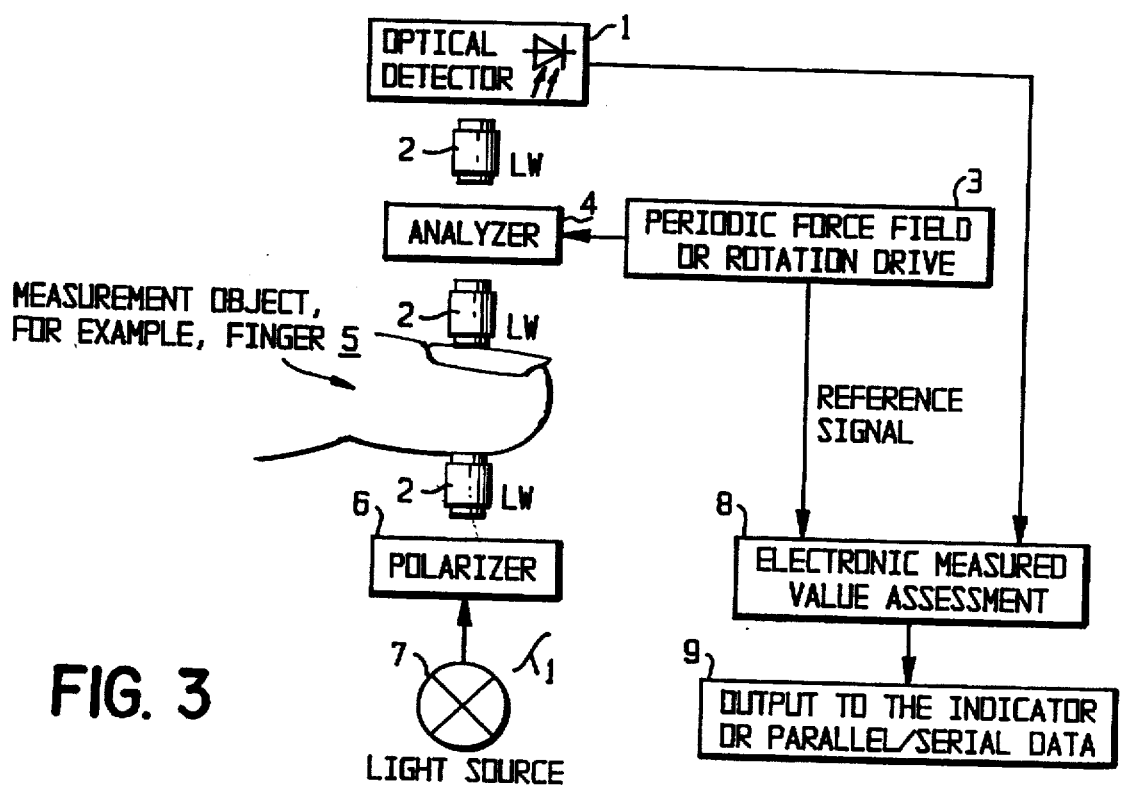
FIG. 3, as an alternative, with periodically changing analyzer, where the reference signal from the force field directly reaches the assessment electronics.
Figure 4:
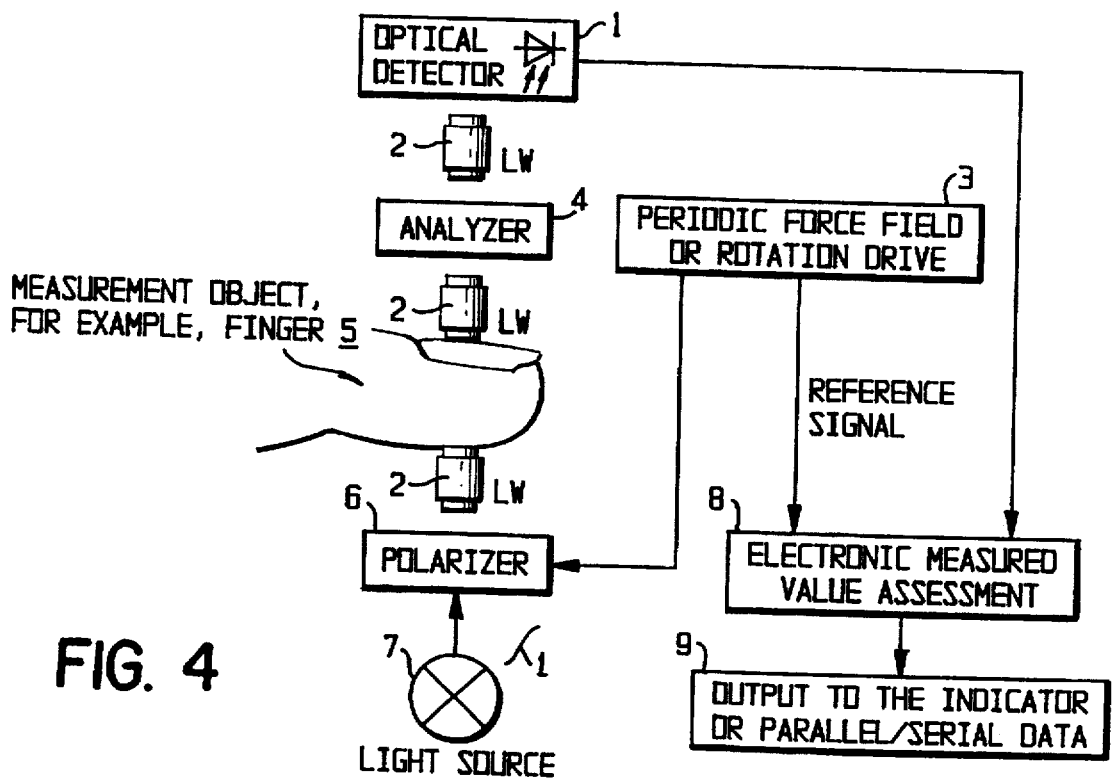
FIG. 4, as an alternative, a periodically changing polarizer, where as well, the reference signal reaches directly from the force field or from the rotation drive to the assessment electronics.
Figure 5:
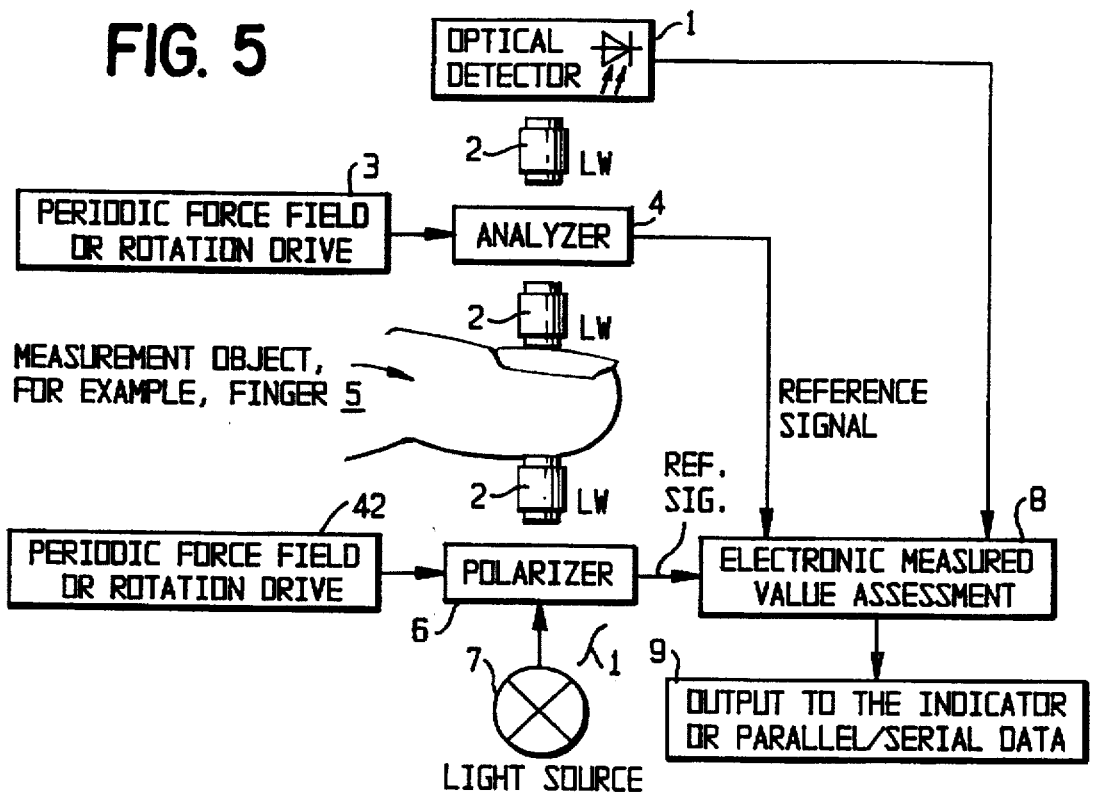
FIG. 5, as an alternative, two changing force fields or rotation drives whose duration of periods must be different (for example, opposite).
Figure 6:
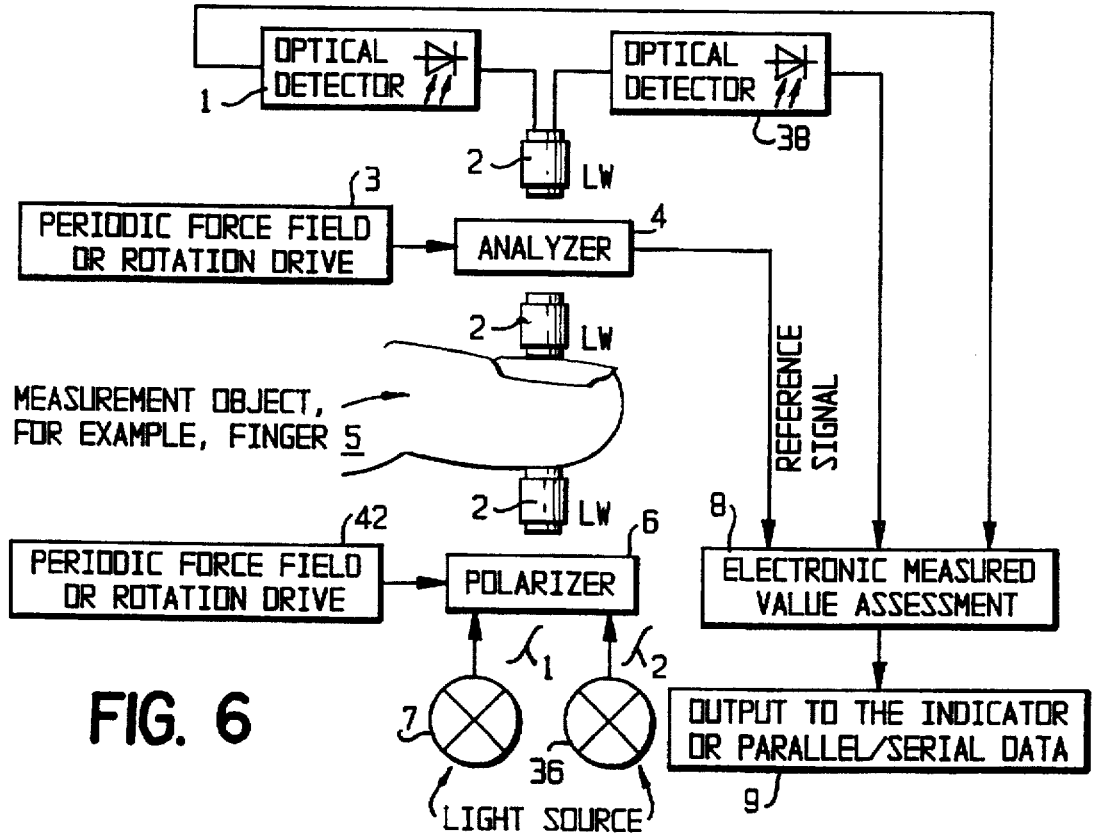
FIG. 6, the possibility of the use of the extinction measurement at several monochromatic light wavelengths.
Figure 7:
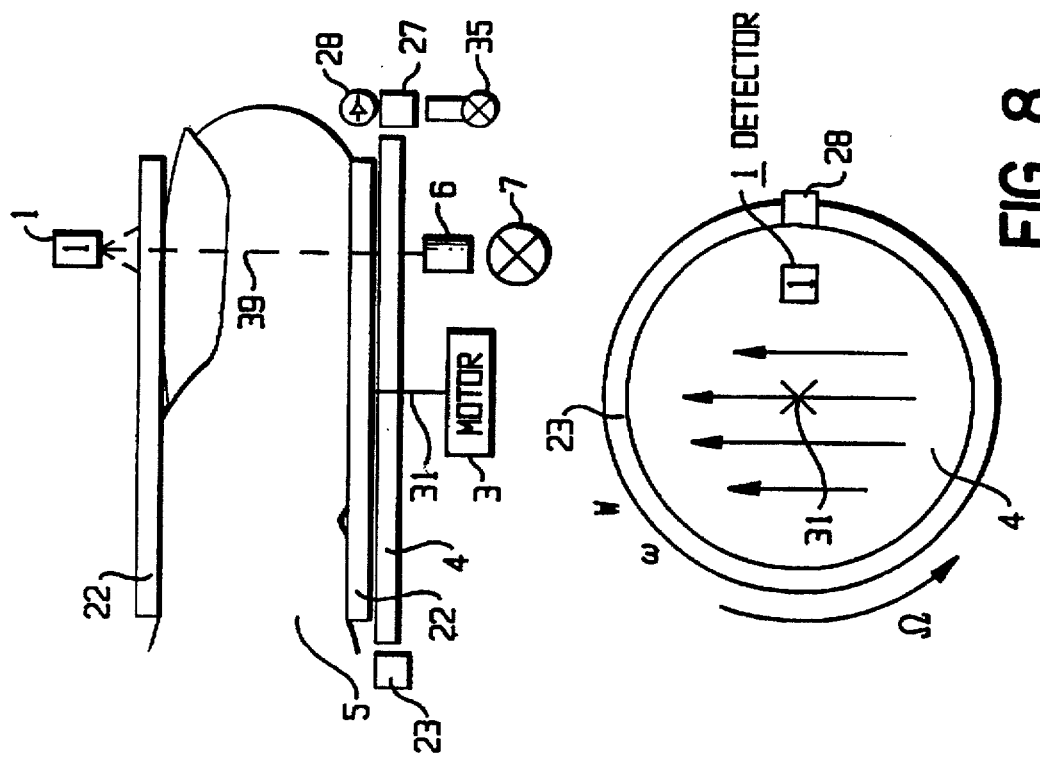
FIG. 7, the practical realization of the measurement device in cross section and in the view from above, for example, on the finger as a measurement object. Different light wavelengths of polarized light can be transmitted in parallel through the measurement object and the rotating analyzer. The analyzer consists of a flat, polarizing disk. On the outer edge of the analyzer disk, the transient phase position is determined through a reference measurement without a measurement object. This phase reference measurement may be optical, electrical, or inductive.
Figure 8:
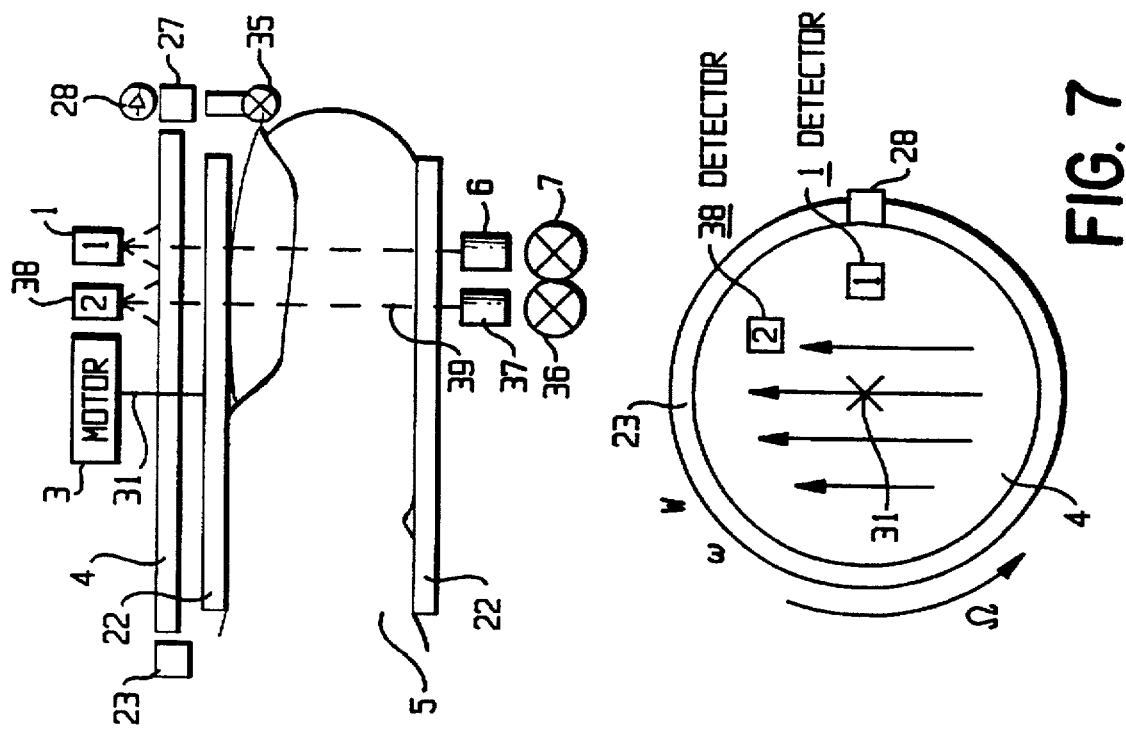
FIG. 8, as an alternative to FIG. 7, the order between the measurement object and the analyzer is switched.
Figure 10:
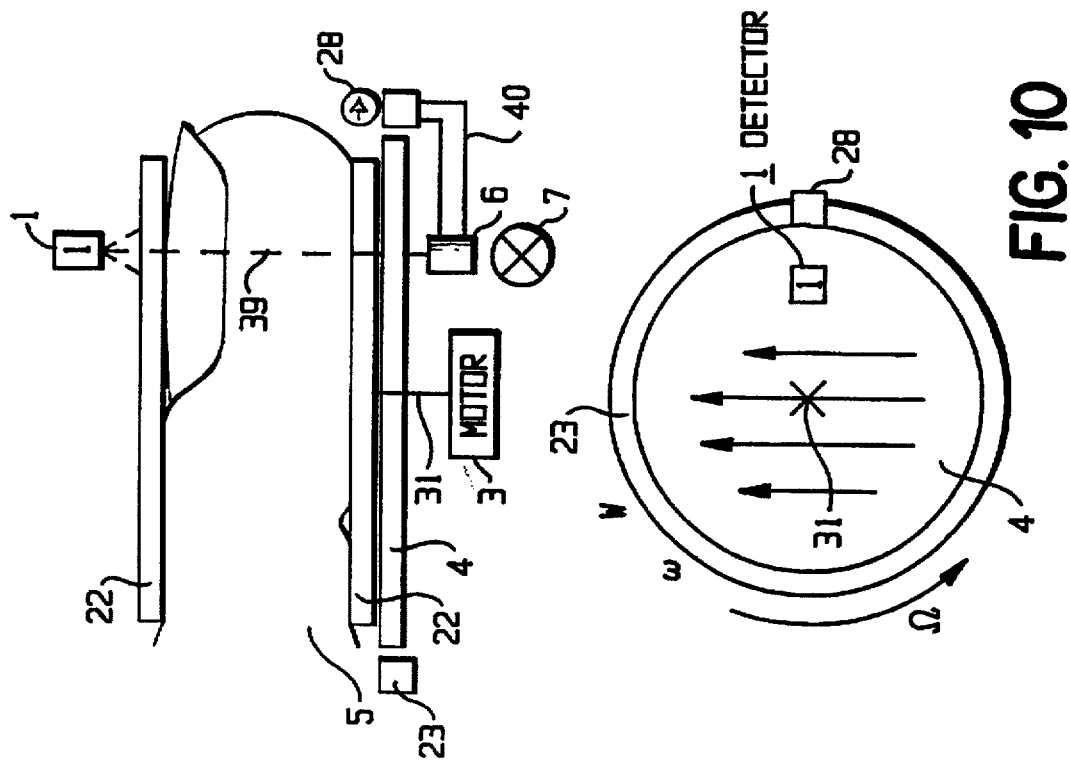
FIG. 10, as an alternative to FIG. 9, the order of the measurement object and analyzer is switched.
Figure 9:
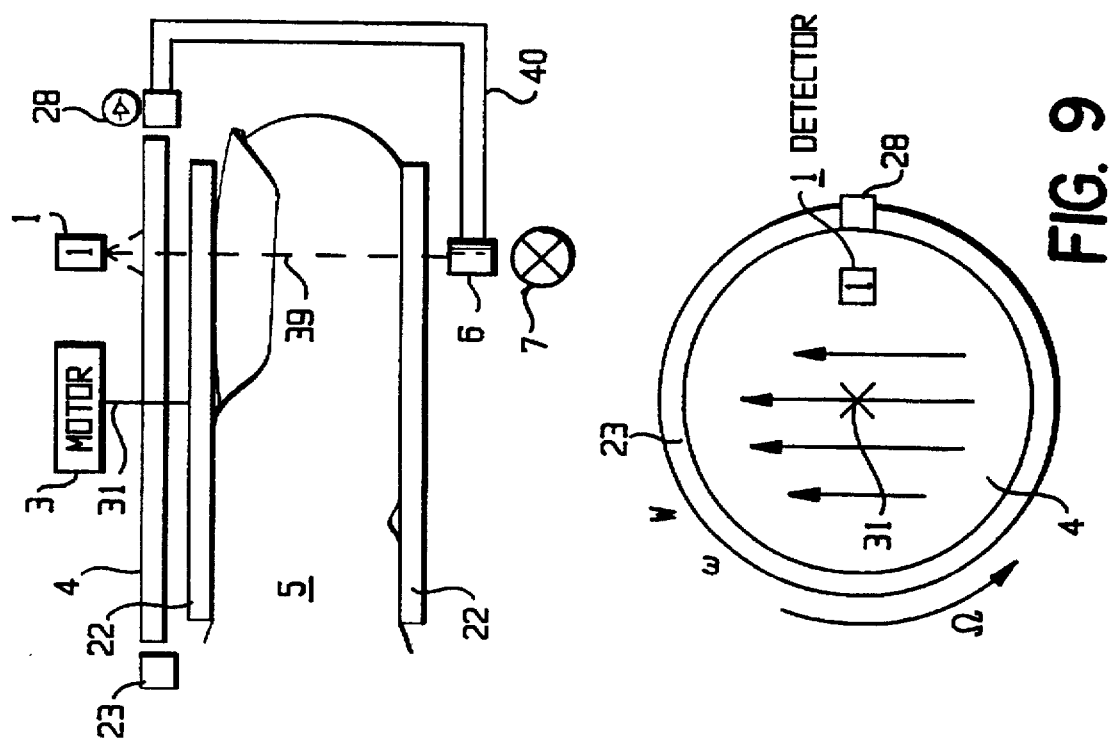
FIG. 9, a waveguide which receives polarization supplies the light for optical reference measurement so that an additional light source can be saved.
Figure 13:
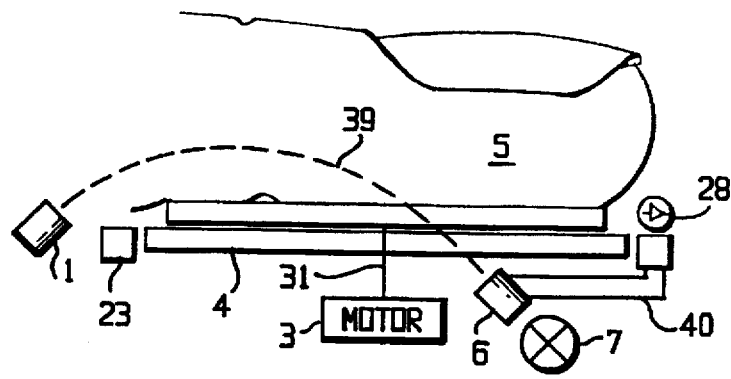
FIG. 13, as an alternative to FIG. 12, where the optical detector and the optical reference detector are stored from one and the same light source. The waveguide here must again receive polarization.

The rotating polarimeter shown in FIGS. 1 to 5 consists of an optical detector (1) and a light source (7) which transmits polarized light through a polarizer (6). The polarized light reaches the measurement object (5) through a waveguide which receives polarization (2) or directly through the airway, and the measurement object is presented here as a finger. Through a periodic force field or a rotation drive (3), an analyzer (4) is periodically influenced so that it continuously changes its angle of polarization.

The detector (1) or the light source (7) individually or together, should be able to send or receive monochromatic light in order to be able to carry out an extinction measurement at the same time as the phase measurement. In order to measure in the blood independently of the oxygen saturation, light wavelengths of approximately 550 nm and approximately 805 nm are particularly suitable. Other monochromatic light wavelengths can also be assessed in parallel with the light source (36), polarizer (37) and optical detector (38). The waveguide (2) must be one which receives polarization. It can also be absent altogether, so that the light is given input or output through the air or directly into the tissue.

The periodically rotating system in each case (4) or (6) supplies a reference signal to the measurement electronics which is not influenced by the measurement objects (5). This reference can also be given directly by the periodic force field/rotation drive (3) to the measurement electronics. From there, it is either displayed directly on a display (9,82) or put on a parallel or serial databus (9,83).

In FIGS. 7 to 13, a practical example of this device with a polarizing analyzer disk (4) is shown. The reference measurement is performed either by the periodically changing polarizer/analyzer itself or is taken, for example, in the case of a polarizing disk, through a separate track (23). The track consists either of the modulating disk itself, of a resistance layer, a ferromagnetic layer, a reflective or transmittent material which delivers a periodic signal in the rotation direction to the attached sensor, whereby the reference track (23) is modulated, for example, in a sinusoidal form or, for example, in a rectangular form in the direction of rotation for the sensor (28). A transparent mechanical holder (22) which receives polarization supports the axis (31), the accompanying analyzer disk (4), and the motor or drive (3) as well as the rest of the assembly. In this concrete assembly, the reference is measured through an optical detector (28). Here, the light reaches the photosensor either directly or through a waveguide which receives polarization (40). The polarized reference light can be generated not directly by the actual light source (6) but rather also through a separate light source (35) with the accompanying polarizer (27). A waveguide (41), which is mounted not anywhere between the polarizer, measurement object, and analyzer, does not need to be capable of receiving polarization.

Figure 14:
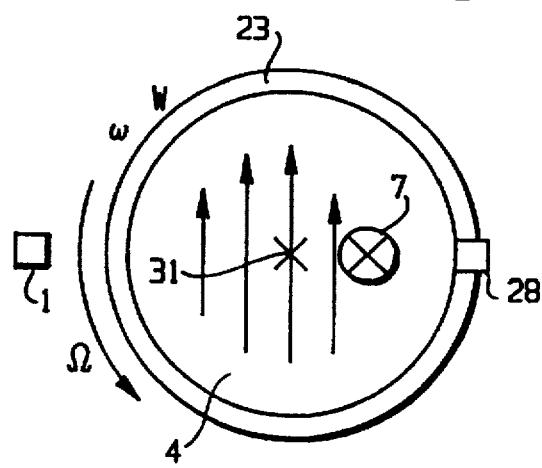
FIG. 14, waveguide which receives polarization both as a transmitter optode (2) and also as reception optode (2 [sic; 51]) in the transmission. The degree of effect of the input and output can be improved through the lens system. This figure shows that using waveguides which receive polarization, the optodes can be applied externally also, for example, for reasons of technical safety, and must not be positioned directly on the measurement device.
Figure 14:
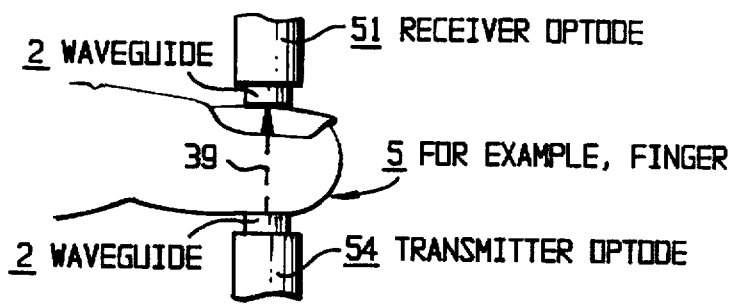
Figure 15:
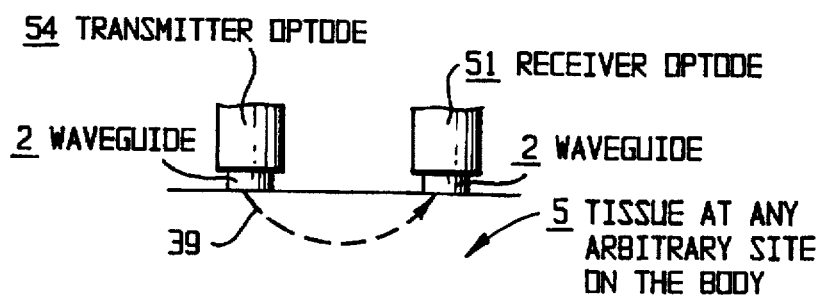
FIG. 15, as alternative to FIG. 14, here a reflectance measurement through a waveguide which receives polarization is indicated, whereby the measurement device also must not necessarily be directly positioned on the measurement object.

In FIGS. 14 and 15, the signal is assessed externally with the waveguides (2) which receive polarization. The transmitter optode (54) and receiver optode (51) are protected against foreign light by an external casing which is impermeable to light and against interference factors and mechanical stress.

Figure 16:
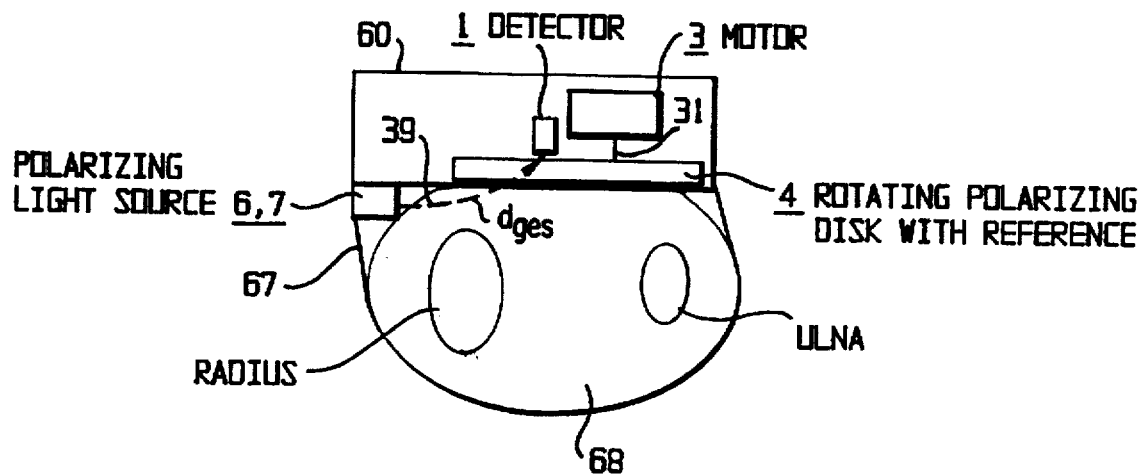
FIG. 16, an armband device which the diabetic can wear continuously like a wristwatch. The housing (60) contains the complete measurement device with battery. The blood sugar measurement device is connected firmly to the arm through an armband (67). Here as well, a rotating polarizing disk (4) is used. Detector and force are exchangeable in each case.
Figure 17:
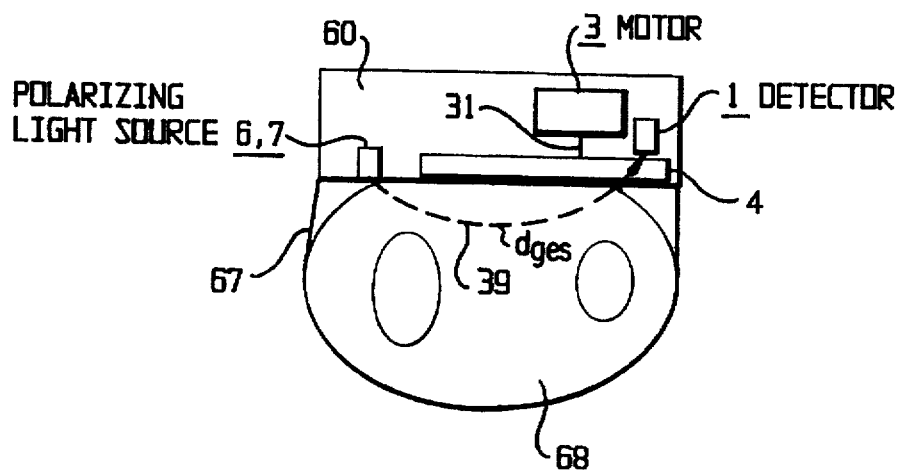
FIG. 17, as alternative to FIG. 16, a reflectance measurement (diffraction measurement) with the armband device. Here, the source and optical detector are also exchangeable.

In FIGS. 16 and 17, the assembly of the device is presented as an armband device. Here, the total device is supported by the housing (60), and the latter is fastened to the arm (68) by the armband (67).

Figure 18:
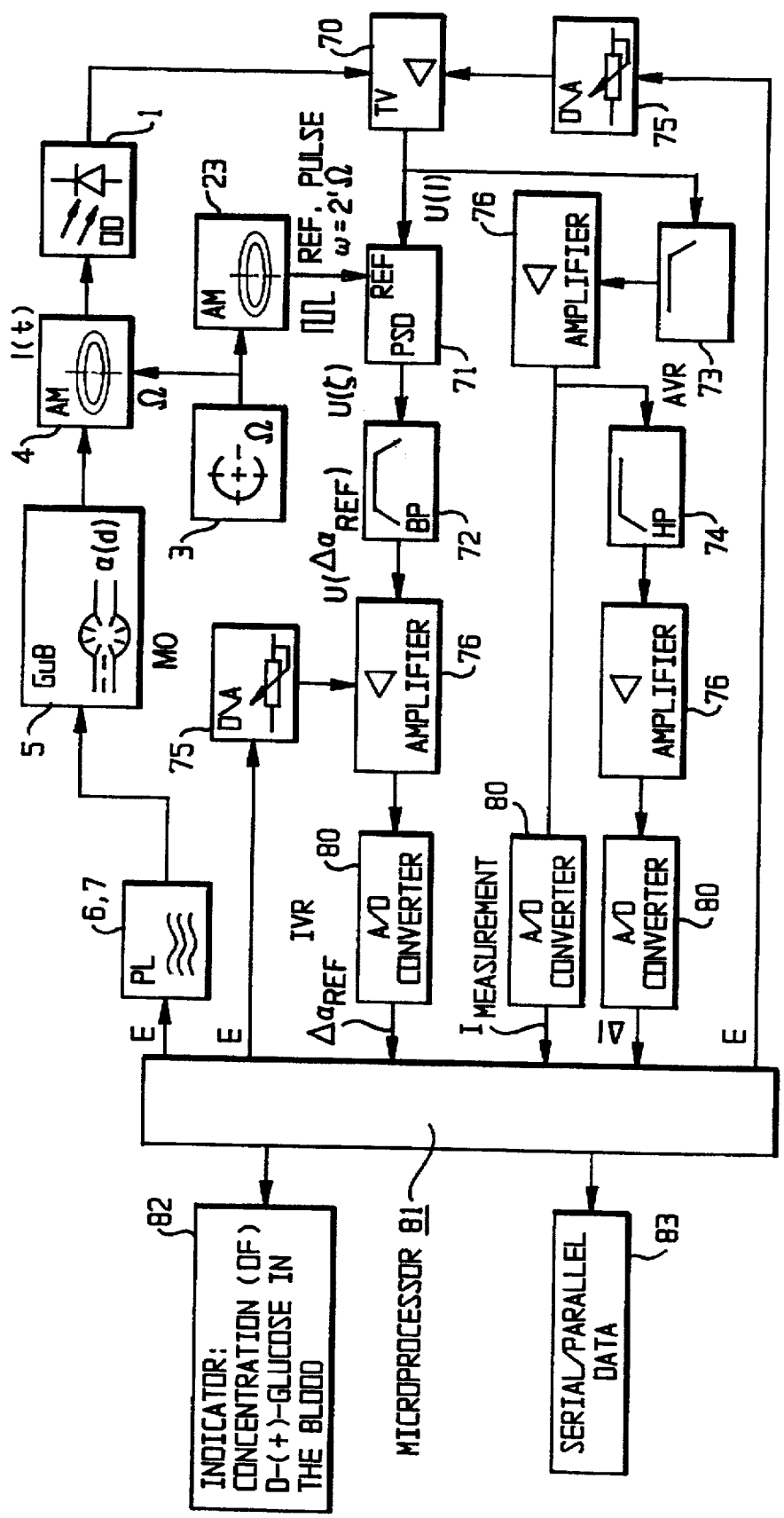
FIG. 18, as block diagram, the complete realization of the measurement device together with the accompanying measurement electronics. To determine the polarization angle, the modulated light is again demodulated through a phase-sensitive detector and measured as voltage level.
Figure 19:
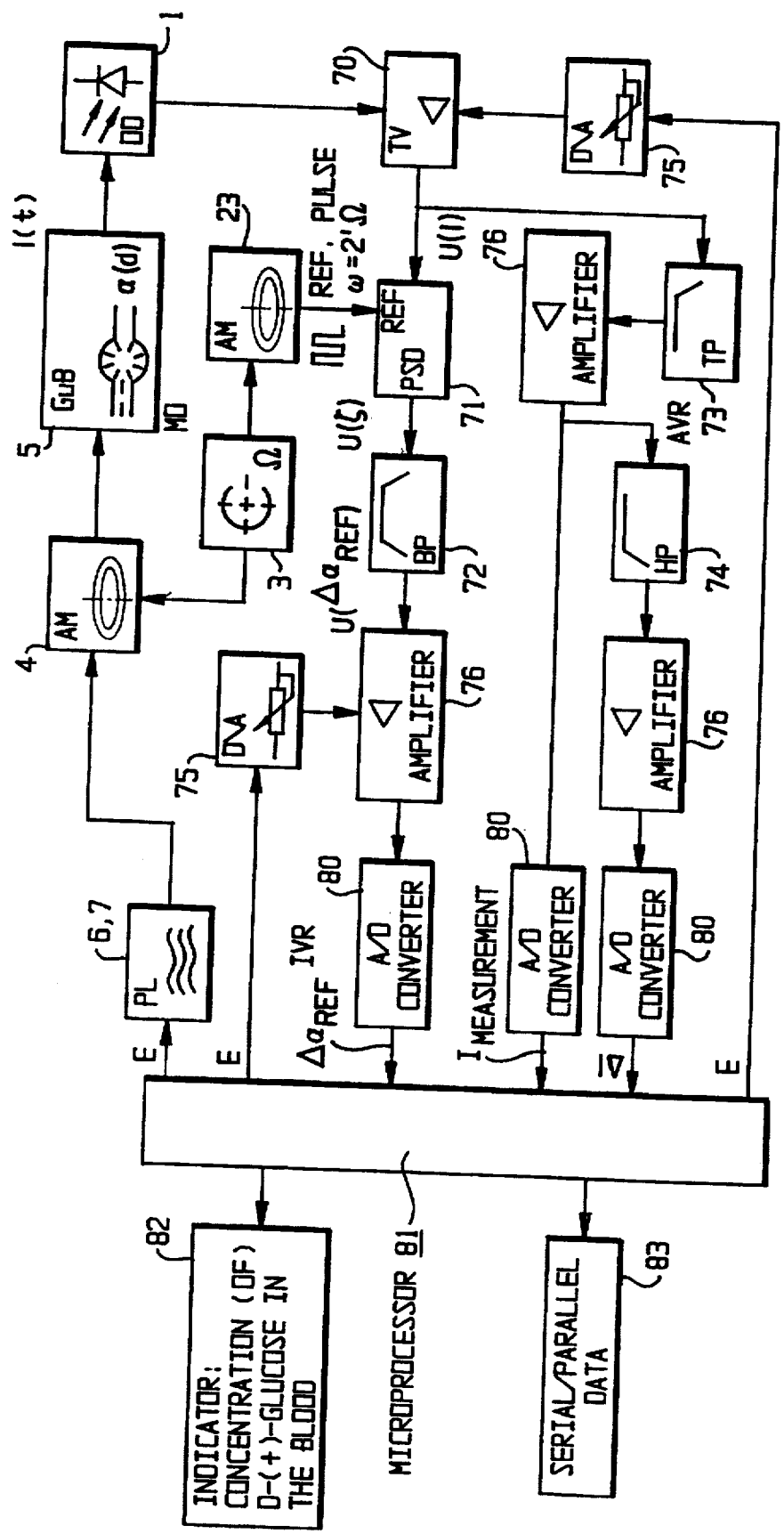
FIG. 19 shows as an alternative to FIG. 18, the block diagram with reverse order. Here, the measurement object is behind the analyzer.

In FIGS. 18 and 19, the electronic measurement assessment of the signal is described. Here, the incoming current is converted into a proportional voltage through a transimpedance amplifier (70). This value is then assessed parallel through three branches and supplied to the microprocessor (81) as digital values. The three individually constructed AD converters (80) stand as examples for a multiplexed AD converter. In the first branch, the voltage level is directed to a bandpass filter (72) through a phase-sensitive detector (PSD) (71) and from there is directed to a programmable amplifier, which is realized here by an amplifier (76) and a D/A converter (75). From there, the voltage is directed to a multiplexed A/D converter (80) proportionally. A parallel branch filters out higher frequency signals through a low-pass filter (73), and amplifies the signal through an amplifier (76). Subsequently, this branch splits into two branches, of which one reaches the multiplexed A/D converter (80) directly. The other branch runs through a high-pass filter (74) and through an amplifier (76) to the multiplexed A/D converter.

Figure 20:
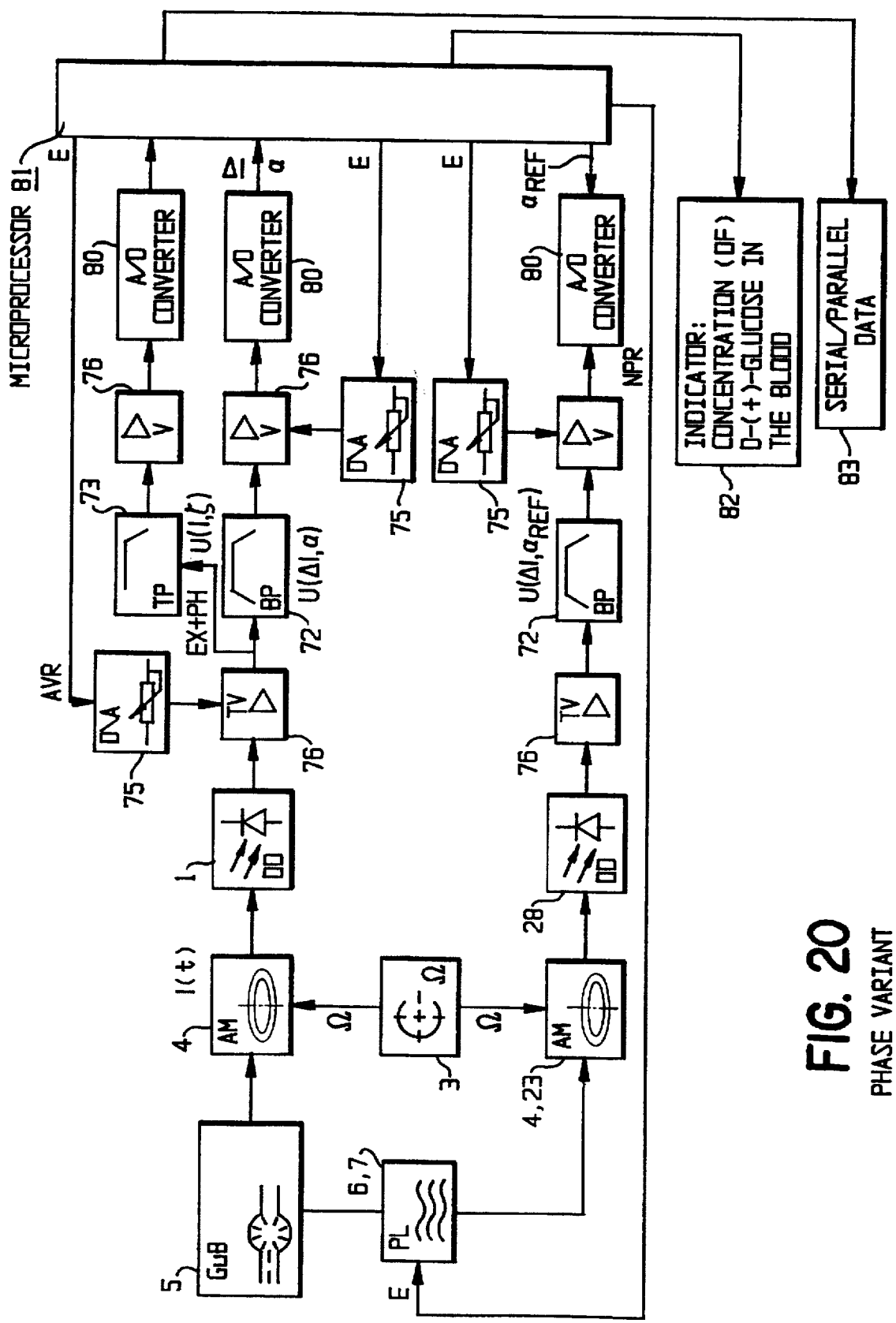
FIG. 20 as block diagram the complete realization of the measurement device together with the accompanying measurement electronics. To determine the angle of polarization, the phase course through the measurement object is compared with the reference phase. For this, the differential phase angle between the two zero throughputs is determined and used to calculate the glucose concentration.
Figure 21:
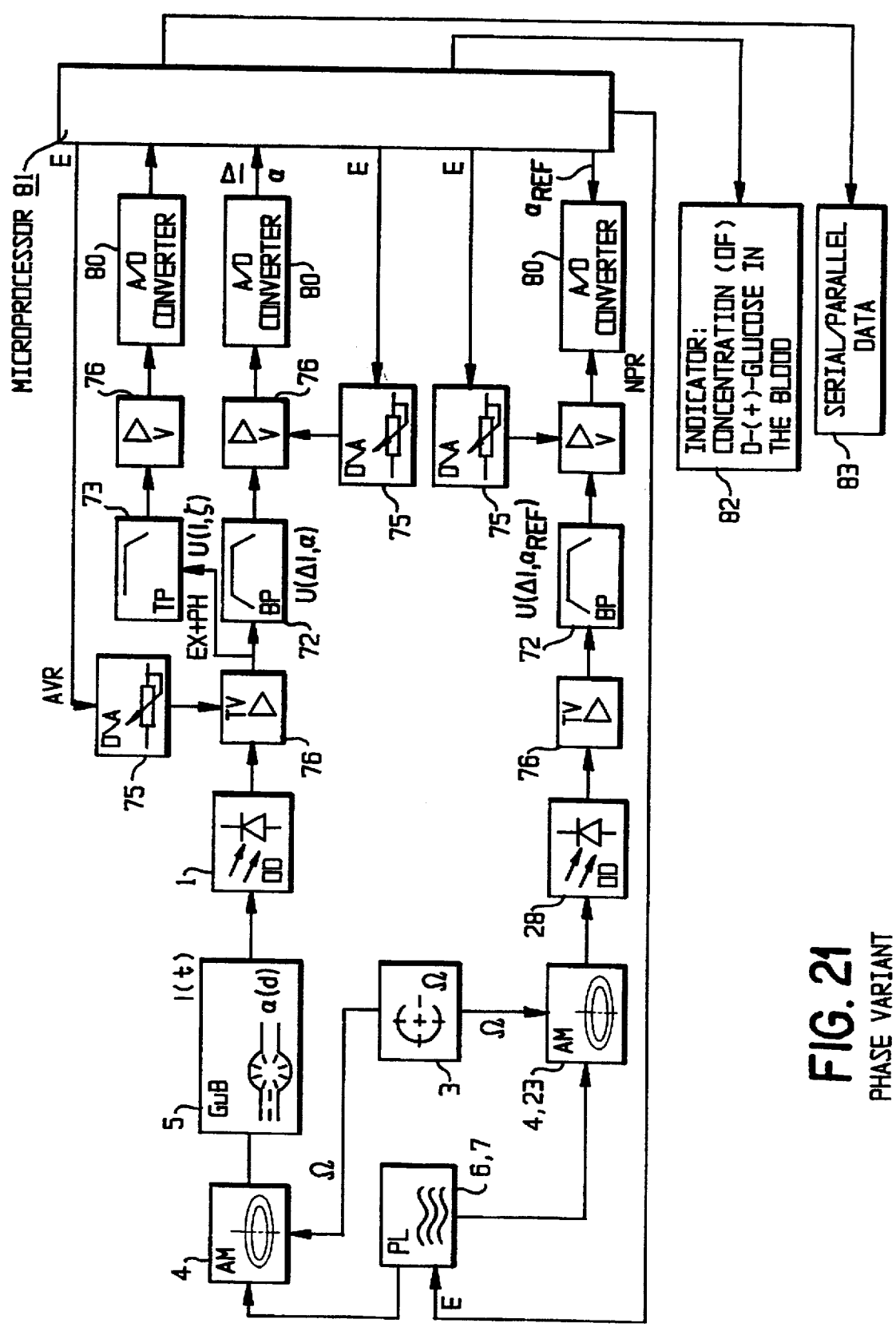
FIG. 21 indicates, as an alternative to FIG. 20, the block diagram with reverse order. Here, the measurement object is behind the analyzer.

In FIGS. 20 and 21, another variant of the electronic measurement assessment is presented. Here, the components named previously are located in part in a changed order. Through the indicator (9,82) the current blood sugar value is displayed. It can also be transmitted as information in the form of serial or parallel or analog data, to other receivers (9,83).

Figure 22:
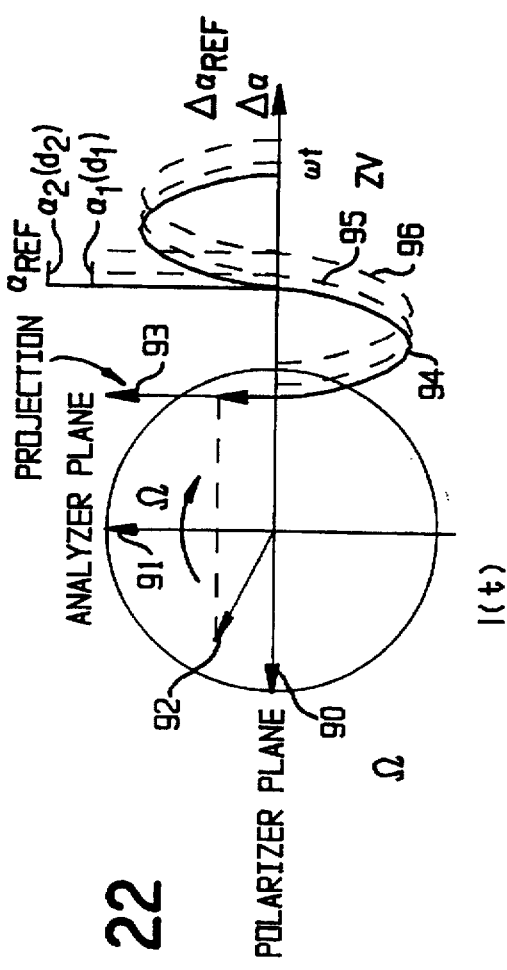
FIG. 22, the conversion of the angle of polarization through the rotating analyzer in a phase angle. The mathematical association is represented here as an illustration.

In FIG. 22, in a visible manner, the generation of the angle modulation of the light intensity through the rotation of the analyzer is presented. If an originally crossed position of polarizer plane (90) to analyzer plane (91) is assumed, the shift of these planes with respect to one another due to the rotation of the analyzer is indicated with a Ω rotating indicator (92). The projection of this indicator on the projection axis (93) indicates the modulation of the light intensity as a function of the indicator position.

Figure 23:
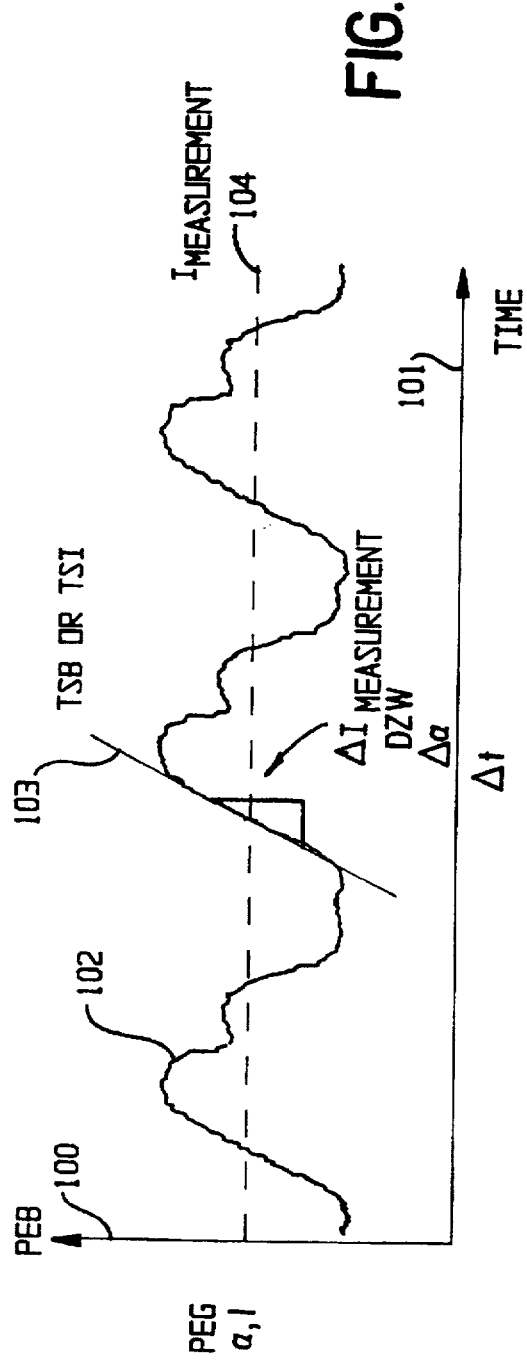
FIG. 23 describes the differential slope of extinction based on blood pulsation and the differentially changed angle of polarization, synchronous to it, caused by the blood sugar.

In FIG. 23, in a visible manner, the electronic assessment of the measurement data both from the extinction and also from the polarization through the axis (100) and through the time axis t (101) is represented schematically. The blood sugar concentration is determined here both through the mean value of the intensity $I_{measurement}$ (104) as well as through the differential slope (103) of the extinction (103) and the polarization (103) from the blood pulsation according to the equation (26). The intensity course (94) indicates the measured reference function course without measurement objects. The function courses (95) and (96) indicate the phase shift of the modulated light based on the blood pulsation under different conditions, determined by the pulsating, changing blood sugar concentration at the sensor.

In the following, two measurement "variants" are explained:

The irradiated, polarized light is modulated through a rotating analyzer and also radiates through the measurement object. The rotating analyzer consists, for example, of a layer of polarization film on a transparent support material which can receive polarization. The analyzer is driven by an electric motor. To compare the phase position of the light falling on the detector to the effective direction of the polarization film, the analyzer has a reference track on it. The reference measurement makes possible a comparison of the phase position with the measurement object to the phase position without measurement objects.

The course of the phase rotation α is modulated through different layer thicknesses of the blood pulse stream. Through extinction measurements (static and dynamic) as well as through polarization measurements (dynamic), the glucose concentration can be determined simultaneously with one and the same sensor, independent of tissue, using electronics. Whereas the extinction measurement, for example, at a wavelength of 805 nm is relatively easy to make, the developed polarimeter with the accompanying reference measurement is required because of the precision necessary for the polarization measurement. To determine the angle of rotation α and thus the sugar concentration C, 2 paths are now available:

I.) Demodulation by means of PSD (phase-sensitive detector) ("demodulator variant"):

The complete measurement assembly is presented in FIGS. 18 and 19.

The high-pass filter connected to the TIV transmits the alternating voltage $U=-U_{max}/2*\cos(\omega t-2\alpha)$ to a "lock-in" amplifier. By demodulation in PSD synchronized with ω (α=0), the result is:

$$U_{PSD}=U_{max}/\pi*\sin(2\alpha)$$

Since the angles which appear are very small, then $\sin(2\alpha)\cong 2\alpha$ applies, that is, also:

$$\alpha = U_{PSD}/(2 * U\text{max}) * \pi \qquad (6)$$

The value $U_{max}\sim I_{max}$ is measured discretely and supplied to the microprocessor for calculation of α or kept constant through a regulatory circuit. Thus, the rotation α corresponding to the light path d is present as voltage $U_{PSD}$.

Motor fluctuations have no effect on the measurement results through the PSD.

The sought angle magnitude of the glucose polarization here is present continuously as a voltage level.

The values are continuously supplied to the A/D converters so that they are available at any time to the microprocessor. Through the digitized voltage levels, the blood sugar concentration can be calculated with a small calculator program according to the formula (6) mentioned above. The necessary extinction values (static and dynamic) are present, after demodulation, again directly as measurement values.

The determination of the glucose concentration is made by a calculator program corresponding to the formulas listed. For this, the static measured value and the differential derivations of the intensity and angle of polarization of the blood pulse are determined at comparable times (for example, slope in the inflection point of the rising blood pulse)

2.) Measurement of the phase shift ("phase variant")

The complete measurement assembly is presented in FIGS. 20 and 21.

Here, the phase shifts are assessed directly. The incoming function course $U(\alpha)$ is phase-shifted with respect to the course for $\alpha=0$ corresponding to the optical activity of the blood sugar and the path d traveled. The phase shift is detected by the zero throughputs of the function courses. On the zero throughputs, the amplification can be selected to be extremely high (calculator controlled), so that the temporal resolution and thus the measurement precision depends now only on the impulse frequency of the microprocessor hardware. For this, the intensity of any distance of the "actual" voltage is adapted from the zero throughput by the calculator program (for example, by companding). The zero throughputs of the input functions can, therefore, be determined with very much greater temporal precision. The absolute polarization angle magnitude of $\alpha(d)$ is determined through the period duration and interval to the reference phase.

The measured value $U(\alpha 1)$ is phase-shifted with respect to the "zero phase reference" $U(\alpha)$ corresponding to the optical activity of the blood sugar. The absolute angle is a result of this phase shift compared to the total period duration. This is proportional to the glucose concentration. The phase difference is indicated by the zero throughputs of the function courses. For this, the amplification at the zero throughputs can be selected to be almost infinitely large (for example, by companding). The relatively small angle difference can be indicated very precisely in this way. For the accompanying statistical extinction measurement, the maximum intensity, for example, is assessed.

The determination of the glucose concentration is made by the calculator program corresponding to the formulas listed. For this, the static measured value is determined, as well as the differential deviations of the intensity and of the angle of polarization of the blood pulse at comparable times (for example, slope at the inflection point of the rising blood pulse).

I claim:

1. A measurement device for noninvasively determining the concentration of polarizing substances in the human body, comprising:
   a source of monochromatic light; and
   means responsive to light from said source for performing both a static extinction measurement and a dynamic polarization measurement to obtain a measurement of the concentration of a predetermined polarizing substance in a selected member of the body;
   said performing means including a detector responsive to light from said source to generate a static excitation measurement signal, a polarizer for receiving monochromatic light from the light source and polarizing the received light, an analyzer responsive to polarized light from the polarizer for producing a dynamic polarization measurement signal indicative of the angle of polarization thereof, at least one of said polarizer and said analyzer being rotatable, means for rotating at least one of the polarizer and analyzer, means for confining light from said polarizer to said analyzer to a distinct light path, means for positioning said selected body member containing said predetermined substance in said light path between the polarizer and the analyzer, angle sensor means for generating a reference signal indicative of influence of the rotating means on angle of polarization without influence of said body member being positioned between the polarizer and the analyzer, means responsive to the dynamic polarization measurement signal and the reference signal for determining the angle of deflection of the polarized signal, and means for determining the concentration from said static excitation measurement signal and said angle of deflection.

2. The measurement device according to claim 1, wherein said source of monochromatic light comprises a light-emitting semiconductor component.

3. The measurement device according to claim 1, wherein said source of monochromatic light comprises a light-emitting laser component.

4. The measurement device according to claim 1, wherein said means for confining light to a distinct path comprises an optical waveguide.

5. The measurement device according to claim 4, wherein said means for confining light to a distinct path comprises an optical waveguide between each of said polarizer and said analyzer and the positioning means for said body member.

6. The measurement device according to claim 1, wherein said analyzer includes a polarizing disk having a track for generating said reference signal.

7. The measurement device according to claim 6, wherein said track comprises a layer of material selected to be responsive to said means for rotating, to generate said reference signal according to whether said rotating means is electrical, mechanical, or magnetic.

8. The measurement device according to claim 1, further including means for shielding the polarizer and the analyzer from light sources other than said source of monochromatic light.

9. The measurement device according to claim 1, wherein said rotating means modulates polarized light impinging on said body member to produce a periodic polarization rotation of one of said analyzer and said polarizer.

10. The measurement device according to claim 1, wherein said means for positioning comprises a wristband.

11. The measurement device according to claim 1, wherein said means for positioning comprises a finger cuff.

12. The measurement device according to claim 1, further including means for suppressing interfering frequencies to enhance sensitivity of the device to said measurement signal.

13. A device-implemented method for noninvasively measuring the concentration of sugar in blood by a device adapted to be wearable by a human subject whose blood sugar is to be measured, said method comprising the steps of generating a beam of monochromatic light, confining the light beam to a predetermined optical path to impinge on a preselected portion of the body of the subject when said device is being worn, polarizing the light beam, and performing both a static extinction measurement using the monochromatic light and a dynamic polarization measurement using the polarized light to obtain a measurement of the concentration of sugar in the blood in said preselected body portion; said step of performing a dynamic polarization measurement including analyzing the polarized light beam after impingement on said body portion while rotating the beam to produce a measurement signal indicative of the angle of polarization thereof, generating a reference signal indicative of influence of rotation of the beam on the angle of polarization thereof in the absence of blood in said optical path, and comparing the measurement signal and the reference signal to determine the angle of deflection of the light beam attributable to the presence of blood sugar in the optical path.

14. The method according to claim 13, wherein the step of confining the light beam to a preselected optical path includes directing the beam through an optical waveguide.

15. The method according to claim 13, wherein the step of rotating the light beam includes using one of an electrical, mechanical, or magnetic means of said device for the rotation.

16. The method according to claim 13, further including the step of shielding the light beam from contribution by other sources of light during generation and along said optical path thereof.

17. The method according to claim 13, further including the step of providing a receptacle in the optical path to enable positioning the preselected body portion therein.

18. The method according to claim 17, wherein said receptacle comprises one of an armband, a wristband, and a finger cuff.

19. The method according to claim 13, wherein the optical path directs the light beam through the preselected body portion to provide a transmission measurement.

20. The method according to claim 13, wherein the optical path directs the light beam obliquely on the preselected body portion for shallow reflection therefrom to provide a reflectance measurement.

21. The method according to claim 13, including:

a) determining the time derivative $\Delta\alpha/\Delta t$ of the rotation of the polarization plane caused by the concentration of sugar in the blood, b) determining the light intensity I at the end of the optical path and the time derivative $\Delta I/\Delta t$ thereof, and c) determining the concentration C of blood sugar as:

$$C = (A)(I)[(\Delta\alpha/\Delta t)(\Delta I/\Delta t)],$$

where A is a constant which is experimentally determined.

* * * * *